(12) United States Patent
Heuermann

(10) Patent No.: US 11,393,653 B2
(45) Date of Patent: Jul. 19, 2022

(54) MEASURING METHOD AND MEASURING DEVICE FOR A LIQUID METAL SLIDE BEARING

(71) Applicant: Siemens Healthcare GmbH, Erlangen (DE)

(72) Inventor: Oliver Heuermann, Adelsdorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/011,061

(22) Filed: Sep. 3, 2020

(65) Prior Publication Data

US 2021/0082654 A1 Mar. 18, 2021

(30) Foreign Application Priority Data

Sep. 12, 2019 (EP) .................................... 19196960

(51) Int. Cl.
| | |
|---|---|
| *H01J 35/10* | (2006.01) |
| *G01N 22/00* | (2006.01) |
| *G01N 23/2251* | (2018.01) |
| *G01N 27/02* | (2006.01) |

(52) U.S. Cl.
CPC ............ *H01J 35/104* (2019.05); *G01N 22/00* (2013.01); *G01N 23/2251* (2013.01); *G01N 27/02* (2013.01); *G01N 2223/07* (2013.01)

(58) Field of Classification Search
CPC .......... H01J 35/00; H01J 35/10; H01J 35/104; G01N 27/02; G01N 22/00; G01N 23/2251; G01N 2223/07; G01N 27/00; G01N 27/06; G01F 23/26; F16C 17/02; F16C 33/6692
See application file for complete search history.

(56) References Cited

U.S. PATENT DOCUMENTS

| | | | |
|---|---|---|---|
| 4,279,149 A | 7/1981 | Block | |
| 5,654,999 A | 8/1997 | Gemmel et al. | |
| 5,668,849 A * | 9/1997 | Sugiura | ................ F16C 17/107 378/133 |
| 2019/0090840 A1 | 3/2019 | Nagesh | |
| 2021/0239456 A1 * | 8/2021 | Nakajima | ........... B29C 48/0018 |

FOREIGN PATENT DOCUMENTS

| | | |
|---|---|---|
| DE | 19510068 A1 | 10/1996 |
| DE | 19605085 A1 | 8/1997 |
| DE | 102015220754 B3 | 2/2017 |
| EP | 0010539 A1 | 4/1980 |
| EP | 3499543 A1 | 6/2019 |
| JP | H05290771 A | 11/1993 |
| WO | WO-2015176861 A1 | 11/2015 |

* cited by examiner

*Primary Examiner* — Jurie Yun
(74) *Attorney, Agent, or Firm* — Harness, Dickey & Pierce, P.L.C.

(57) ABSTRACT

A measuring method for a liquid metal slide bearing is disclosed. In at least one embodiment, the measuring method includes providing a liquid metal slide bearing to be measured, the liquid metal slide bearing including two bearing parts with liquid metal being arranged between the two bearing parts. The method further includes measuring inductance, or a variable associated with the inductance, of the liquid metal slide bearing; and determining a quantity of liquid metal in the liquid metal slide bearing based upon the inductance, or the variable associated with the inductance, measured. Furthermore, a corresponding measuring device, a liquid metal slide bearing and an x-ray tube and an apparatus are disclosed.

21 Claims, 4 Drawing Sheets

MEASURING METHOD AND MEASURING DEVICE FOR A LIQUID METAL SLIDE BEARING

PRIORITY STATEMENT

The present application hereby claims priority under 35 U.S.C. § 119 to European patent application number EP 19196960.9 filed Sep. 12, 2019, the entire contents of which are hereby incorporated herein by reference.

FIELD

Embodiments of the invention generally relate to a measuring method and measuring device for a liquid metal slide bearing with a rotating and a fixed bearing part, between which a bearing gap filled with liquid metal is located. The measuring device or the measuring method can be used to determine the fill level of the liquid metal slide bearing with liquid metal.

BACKGROUND

Liquid metal slide bearings (also simply referred to below as "slide bearing" or "bearing") are frequently used in the technical field of rotary anode tubes, in particular in expensive apparatuses in computed tomography and angiography. They can however also be used in the field of radiology, surgery and mammography. Liquid metal slide bearings in x-ray tubes are used, for instance, to support the rotary anode and are typically located in the inside of the vacuum housing of the x-ray tube.

Gallium, indium or tin alloys, which are already liquid at room temperature, are generally used as liquid metal. The liquid metal used is preferably an alloy made from gallium, indium and tin. It is manufactured and marketed by the company Geratherm Medical AG under the brand name Galinstan.

Nowadays the liquid metal fill level of a slide bearing is measured with the aid of a high-energy NDT scanner (NDT: "Non Destructive Testing"). An electron accelerator system which generates photons in the energy range of a few MeV (megaelectron volt) is typically used here. One example of this is a system known under the name "SILAC" (Siemens Industrial Linear Accelerator) with a photon energy in the range of 6 to 9 MeV. In most cases this test is carried out after the filling process and before further manufacturing processes of the bearing and is both time-consuming and also expensive. Such a test is however very meaningful and is basically only restricted by the available image resolution.

SUMMARY

It is naturally also easily possible to record the overall weight of a bearing before and after the filling process (and possibly to weigh it again in order to check the fill level or to reduce statistical errors), or to use the measured values as a reference for bearings constructed in the same way. The inventors have discovered, however, that this is disadvantageous in that such a measurement can have serious errors since the weight of each individual bearing part and thus also its deviation from a standard weight is included in the measurement.

At least one embodiment of the present invention specifies an alternative, more convenient measuring method and a corresponding measuring device for liquid metal slide bearings (for their fill level), with which the disadvantages described above are avoided. In particular, one embodiment of the invention specifies a measuring method or a measuring device, which allow(s) a pre-evaluation of the fill level (e.g. full, half full, empty), preferably after the filling process or even during the filling process in the vacuum.

Embodiments include a measuring method, a measuring device, a liquid metal slide bearing, an x-ray tube and an apparatus.

In at least one embodiment, the inventive measuring method for a liquid metal slide bearing is used to measure the quantity of liquid metal in the liquid metal slide bearing and comprises:

providing a liquid metal slide bearing to be measured, this liquid metal slide bearing here has two bearing parts, between which the liquid metal is arranged;

measuring the inductance of the liquid metal slide bearing or a variable associated with the inductance; and determining the quantity of liquid metal in the liquid metal slide bearing on the basis of the inductance or the variable associated with the inductance.

In at least one embodiment, the measuring device comprises:

a measuring unit designed for measuring the inductance of the liquid metal slide bearing or a variable associated with the inductance;

a determination unit designed for determining the quantity of liquid metal in the liquid metal slide bearing on the basis of the inductance or the variable associated with the inductance.

An inventive liquid metal slide bearing of at least one embodiment comprises two bearing parts, between which the liquid metal is arranged, preferably an inner bearing part and an outer bearing part, between which a bearing gap filled with liquid metal is located. The liquid metal slide bearing is designed here to connect a measuring unit of an inventive measuring device. One of the bearing parts preferably comprises an electrical contact for connecting an RF unit/RF generator of the measuring device and the other bearing part comprises an electrical contact for connecting a measuring unit of the measuring device.

An inventive x-ray tube comprises a rotary anode, which is rotatably supported by way of an inventive liquid metal slide bearing of at least one embodiment.

An inventive apparatus of at least one embodiment, in particular designed for examination by way of x-ray radiation, comprises an inventive measuring device and/or is designed to carry out an inventive measuring method and/or comprises an inventive liquid metal slide bearing. The apparatus is preferably a medical apparatus, e.g. an x-ray apparatus or a computed tomography apparatus.

An inventive apparatus of at least one embodiment, in particular designed for examination by way of x-ray radiation, comprises an inventive measuring device of at least one embodiment and/or is designed to carry out an inventive measuring method of at least one embodiment and/or comprises an inventive liquid metal slide bearing of at least one embodiment. The apparatus is preferably a medical apparatus, e.g. an x-ray apparatus or a computed tomography apparatus.

At least one embodiment of the invention therefore also comprises a computer program product with a computer program which can be loaded directly into a storage facility of a measuring device or an apparatus, having program portions in order to carry out all essential steps of the method according to at least one embodiment of the invention (the determination) when the computer program is executed in the measuring device or the apparatus.

At least one embodiment of the invention thus also comprises a computer-readable medium, on which program portions that can be read in and executed by a computer unit are stored, in order to carry out all steps of the method according to at least one embodiment of the invention when the program portions are executed by the computer unit.

At least one embodiment of the invention is directed to a measuring method for a liquid metal slide bearing, comprising:

providing a liquid metal slide bearing to be measured, the liquid metal slide bearing including two bearing parts with liquid metal being arranged between the two bearing parts;

measuring inductance, or a variable associated with the inductance, of the liquid metal slide bearing; and determining a quantity of liquid metal in the liquid metal slide bearing based upon the inductance, or the variable associated with the inductance, measured.

At least one embodiment of the invention is directed to a measuring device for a liquid metal slide bearing including two bearing parts, liquid metal being arranged between the two bearing parts, the measuring device comprising:

a measuring unit, designed to measure inductance of the liquid metal slide bearing or a variable associated with the inductance; and a determination unit, designed to determine a quantity of liquid metal in the liquid metal slide bearing based upon the inductance, or the variable associated with the inductance, measured.

At least one embodiment of the invention is directed to a liquid metal slide bearing comprising:

an inner bearing part; and an outer bearing part, a bearing gap between the inner bearing part and the outer bearing part being filled with liquid metal, wherein the liquid metal slide bearing is configured with contacts designed for connecting with the measuring device of at least one embodiment.

At least one embodiment of the invention is directed to x-ray tube, comprising:

a rotary anode, rotatably mounted via the liquid metal slide bearing of at least one embodiment.

At least one embodiment of the invention is directed to an apparatus, comprising:

the liquid metal slide bearing of at least one embodiment and the measuring device of at least one embodiment.

BRIEF DESCRIPTION OF THE DRAWINGS

The invention is explained in more detail again with reference to the appended figures on the basis of example embodiments. In the various figures, the same components are identified with identical reference signs. The figures are generally not to scale. The drawings show.

DETAILED DESCRIPTION OF THE EXAMPLE EMBODIMENTS

Figure 1:
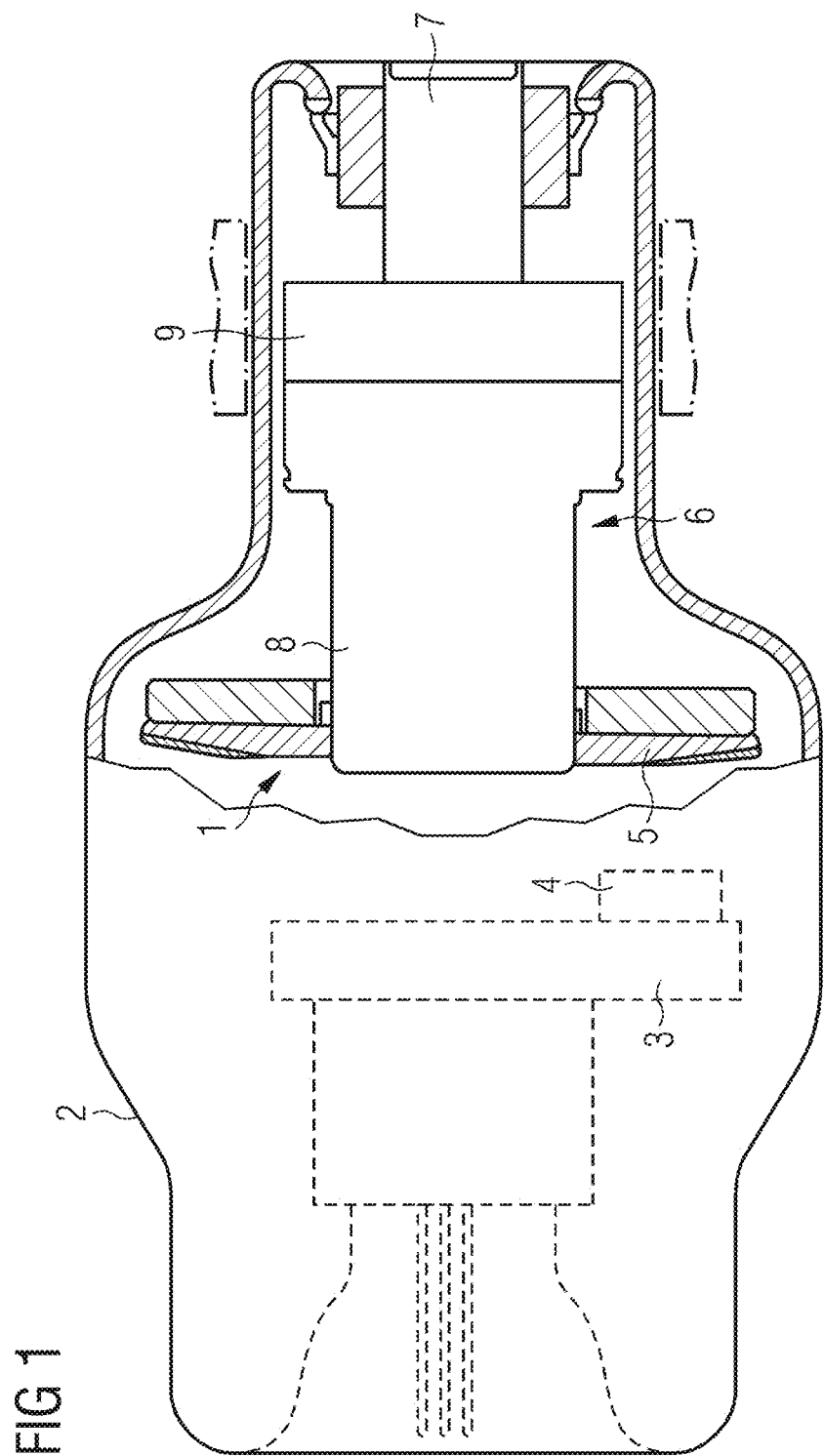
FIG. 1 a longitudinal section through a rotary anode x-ray tube with an embodiment of an inventive liquid metal slide bearing for the rotary anode in a partially cut-out representation, FIG. 2 a longitudinal section through a liquid metal slide bearing, FIG. 3 an example circuit for a model of an embodiment of the invention, FIG. 4 a block diagram for a possible course of an embodiment of the inventive method, FIG. 5 a representation of possible RF signals.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment, the inventive measuring method for a liquid metal slide bearing is used to measure the quantity of liquid metal in the liquid metal slide bearing and comprises:

providing a liquid metal slide bearing to be measured, this liquid metal slide bearing here has two bearing parts, between which the liquid metal is arranged; and measuring the inductance of the liquid metal slide bearing or a variable associated with the inductance;

determining the quantity of liquid metal in the liquid metal slide bearing on the basis of the inductance or the variable associated with the inductance.

One such liquid metal slide bearing typically comprises an inner bearing part and an outer bearing part and a bearing gap filled with liquid metal. The bearing could also be notionally split so that it has a rotating and a fixed bearing part, between which the bearing gap filled with liquid metal is located. The circumferential bearing part (in other words the outer bearing part) can subsequent to the bearing gap have an annular collection groove, which collects liquid metal escaping from the bearing gap. Galinstan (see above) can be used as liquid metal, for instance.

In practice, the measuring of the inductance typically means the inductance of the inner bearing part, of the outer bearing part and of the bearing gap filled with liquid metal. It is basically sufficient to measure the inductance of the bearing gap on its own, if this is possible. In principle, the inductance of the bearing gap (with the liquid metal) should here be determined on its own (see embodiments relating to the following step) but in practice this is problematic or even impossible.

It is often difficult to measure the inductance of the bearing directly. It is therefore possible to benefit from the fact that the inductance can be determined from the (complex) impedance. This impedance (a variable associated with the inductance) can be measured directly or determined by way of a resonance (likewise a variable associated with the inductance).

The method further includes determining the quantity of liquid metal in the liquid metal slide bearing on the basis of the inductance or the variable associated with the inductance.

If the overall inductance $L_G$ of the liquid metal slide bearing is known, the well-known inductances of the bearing parts $L_{Ti}$, $L_{Ta}$ can be deducted. In a model which comes very close to reality, the structure corresponds to the inductances of the bearing parts $L_{Ti}$, $L_{Ta}$ and the bearing gap $L_S$ of a series connection and the inductance of the bearing gap $L_S$ is produced from $L_S = L_G (L_{Ti} + L_{Ta})$. The measured inductance (in other words generally the overall inductance $L_S$) is also referred to as "leakage inductance".

As has already been indicated, the measurement of a resonance frequency $f_R$ is a practical option for determining the overall inductance $L_G$ of the bearing, whereby formula (1)

$$f_R = \frac{1}{2\pi\sqrt{LC_K}} \quad (1)$$

applies with the measured inductance L (generally the overall inductance $L_G$) and the known resonance circuit capacitance $C_K$. The resonance capacitance as a component is calculated and built specially (lies in the region of 10 fP) and checked with a precision measuring bridge. Such reference capacitances are often also an integral part of the measuring bridge calibration. This embodiment of the method is explained in further detail below. It is also possible, however, to determine impedance minima or maxima of the bearing with an impedance analyzer.

To this end it should be noted that the leakage inductance of a liquid metal slide bearing is very small (approx. a few tens to a hundred nH). The resonance frequency therefore typically lies in the VHF to UHF range (e.g. between 150 MHz and 2000 MHz).

In order to determine the amount of liquid metal, the bearing is assumed to be an electric conductor with an overall inductance which depends on the fill level. Here, the concept is assumed that the liquid metal in the bearing gap is comparable to a parallel connection of a number of structural elements. An elementary current path can be considered to be a structural element, which leads from the outer bearing (external bearing part) via the bearing gap to the inner bearing (internal bearing part).

A structural element can be considered to be an independent inductance, wherein a structural element can additionally also have other properties (such as e.g. additionally an ohmic part). The higher the liquid metal level in the bearing gap, the more structural elements are connected in parallel. The more structural elements are connected in parallel, the lower the resulting inductance of the bearing gap LS and thus also the leakage inductance (measured inductance or overall inductance). The inductance of the bearing gap $L_S$ can therefore be considered with the formula (2)

$$L_S = \frac{1}{\frac{1}{L_1} + \frac{1}{L_2} + \ldots + \frac{1}{L_n}} \quad (2)$$

to be an inductance composed of the inductances of the structural elements $L_i$. These $L_i$ can all be the same, in reality these $L_i$ are however in most cases different on account of the design of the bearing.

If the bearing is always aligned the same during a measurement (and no air bubbles are located in the liquid metal), it can be assumed that the $L_i$ of $L_i$ are connected in parallel as far as a specific value n. Here the value "n" is a measure of the fill level. If the fill level is low, in other words the number of structural elements connected in parallel, n is therefore also low and vice versa. The fill level can therefore be determined according to the formula (3)

$$\frac{1}{L_S} = \sum_1^n \frac{1}{L_i} \quad (3)$$

wherein this formula has to be resolved to n. With similar $L_i$ this is easily possible, with in each case different $L_i$ a table of the (known) values for $L_i$ can be used, for instance.

It would also be possible to use a continuous function L(h) in place of the $L_i$, wherein h can be the height of the fill level or a height coordinate relative to the fill level.

An inventive measuring device of an embodiment is used to measure a liquid metal slide bearing, in other words to measure the quantity of liquid metal in the bearing. The liquid metal slide bearing comprises two bearing parts, between which the liquid metal is arranged, in particular an inner bearing part, an outer bearing part and a bearing gap filled with liquid metal.

In at least one embodiment, the measuring device comprises:

a measuring unit designed for measuring the inductance of the liquid metal slide bearing or a variable associated with the inductance;

a determination unit designed for determining the quantity of liquid metal in the liquid metal slide bearing on the basis of the inductance or the variable associated with the inductance.

An inventive liquid metal slide bearing of at least one embodiment comprises two bearing parts, between which the liquid metal is arranged, preferably an inner bearing part and an outer bearing part, between which a bearing gap filled with liquid metal is located. The liquid metal slide bearing is designed here to connect a measuring unit of an inventive measuring device. One of the bearing parts preferably comprises an electrical contact for connecting an RF unit/RF generator of the measuring device and the other bearing part comprises an electrical contact for connecting a measuring unit of the measuring device.

An inventive x-ray tube comprises a rotary anode, which is rotatably supported by way of an inventive liquid metal slide bearing of at least one embodiment.

An inventive apparatus of at least one embodiment, in particular designed for examination by way of x-ray radiation, comprises an inventive measuring device of at least one embodiment and/or is designed to carry out an inventive measuring method of at least one embodiment and/or comprises an inventive liquid metal slide bearing of at least one embodiment. The apparatus is preferably a medical apparatus, e.g. an x-ray apparatus or a computed tomography apparatus.

In summary, it can be said that a special feature of the invention is that the liquid metal slide bearing is considered from an electrotechnical point of view, namely as a coaxial arrangement filled with liquid metal. The scatter parameter values of the bearing are detected electrically in accordance with the invention in order to conclude the liquid metal fill level therefrom. Calibration of the measuring method can take place for instance by a completely filled bearing, which is secured with an electron accelerator system scan, in particular with a SILAC scan (Siemens Industrial Linear Accelerator), being measured. This value of the fill level then represents the reference for the following comparative measurements.

Most of the aforementioned components of the measuring device can be realized entirely or partially in the form of software modules in a processor of a corresponding measuring device. An implementation largely in software has the advantage that even measuring devices already in use can be easily upgraded by a software update in order to work in the manner according to at least one embodiment of the invention.

In this respect, at least one embodiment of the invention is also directed to a corresponding computer program product with a computer program which is loadable directly into a computing system of a measuring device, having program portions in order to carry out all the steps of the method according to at least one embodiment of the invention when the program is executed in the computing system. Such a computer program product can comprise, where relevant, in addition to the computer program, further constituents, such as, for example, documentation and/or additional components including hardware components, for example, hardware keys (dongles, etc.) in order to use the software.

For transport to the computing system and/or for storage at or in the computing system, at least one embodiment of the invention is also directed to a computer-readable medium, for example a memory stick, a hard disk or another transportable or firmly installed data carrier, on which the program portions of the computer program which are readable and executable by a computing system are stored. For this purpose, the computer unit can have, for example, one or more cooperating microprocessors or the like.

At least one embodiment of the invention therefore also comprises a computer program product with a computer program which can be loaded directly into a storage facility of a measuring device or an apparatus, having program portions in order to carry out all essential steps of the method according to at least one embodiment of the invention (the determination) when the computer program is executed in the measuring device or the apparatus.

At least one embodiment of the invention thus also comprises a computer-readable medium, on which program portions that can be read in and executed by a computer unit are stored, in order to carry out all steps of the method according to at least one embodiment of the invention when the program portions are executed by the computer unit.

Further, particularly advantageous embodiments and developments of the invention are given in the claims and in the following description, wherein the claims in one category of claims can also be developed in a similar way to the claims and passages of the description in another category of claims, and in particular individual features of different example embodiments or variants can also be combined to create new example embodiments or variants.

In theory, with respect to the method it essentially makes no difference where the measurement takes place (e.g. where an RF alternating current flows and where the measuring tap is disposed), provided only that sufficient current paths lead through the bearing gap. In practice, limits are however often set. One of these limits is that the liquid metal is located in the inside of the bearing and can essentially not be contacted directly, otherwise it would be ideal to arrange a measuring tap directly on or above the bearing gap, in other words directly on the liquid metal. This is generally practically impossible, however. In practice the inductances of the outer and inner bearing are therefore generally included in the measurement. The values for the inductances of these bearing parts $L_{Ti}$, $L_{Ta}$ are very stable on account of their narrow geometric tolerances. The width of the bearing gap between the outer and inner bearing typically lies in the μm range. With an optimally filled bearing this narrow gap should be filled with liquid metal, so that the bearing is sufficiently load-bearing under operating conditions.

According to a preferred measuring method, an RF alternating voltage is applied between electrical contacts to different bearing parts with a predetermined frequency range. A measurement of an RF signal is then carried out on electrical contacts on different bearing parts. These contacts can theoretically be the same, to which the RF alternating voltage was applied (at least if the RF alternating voltage was applied by way of a resistance). The quantity of liquid metal is then determined on the basis of the measured RF signal.

To this end a preferred measuring device comprises an RF unit designed to apply an RF alternating voltage between electrical contacts to different bearing parts with a predetermined frequency range, a measuring unit designed to measure an RF signal on an electrical contact (or on two electrical contacts on different bearing parts) and a determination unit designed to determine the quantity of liquid metal on the basis of the measured RF signal. The RF unit is not absolutely necessary here and can feasibly be left out. In this case, an external RF unit must be used for a measurement, however.

It is noted that applying an alternating voltage on account of the ohmic law means the same as introducing an alternating current into the bearing. In order to measure the RF alternating voltage on the same electrical contacts, an ohmic resistance can be connected in series with the source of the RF voltage. The resistance separates the signal source from the bearing to be tested. In the series resonance, the current flow through the real part generates a drop in voltage by way of the resistance. The voltage minimum with respect to the signal source can then be measured. The voltage is then preferably measured by way of this resistance or by way of the series connection of resistance and RF unit. The contacts can however theoretically also be positioned so that the ohmic resistance of the bearing gap is utilized. Here the RF alternating current introduced must penetrate the bearing gap filled with liquid metal. To this end, a potential difference should exist between the two bearing parts. The RF alternating current should also penetrate as much liquid metal as possible, in order to generate a drop in voltage. This is advantageous since this mirrors the inductive reactance, from which the inductance can be easily determined.

According to a preferred measuring method, a resonance frequency is determined from the measurement and then the quantity of liquid metal is determined on the basis of the resonance frequency. This can take place e.g. according to the formula (1), wherein the formula is resolved according to the measured inductance L (generally this is the overall inductance $L_S$) and the (constant) inductances of the bearing parts are deducted. It then applies that $L_S$ is in inverse proportion to the square of the resonance frequency $f_R$. Ultimately the measured resonance frequency $f_R$ for determining the quantity of liquid metal and thus the liquid metal state in the bearing gap can therefore also be compared with a value of a value table or a curve.

According to a preferred measuring method, a minimum (in series resonance) or a maximum (in parallel resonance) of the bearing impedance is determined from the measurement and the quantity of liquid metal is then determined on the basis of the bearing impedance.

According to a preferred measuring method, the quantity of liquid metal is determined on the basis of a ratio of the amplitude and the phase of the measured RF signal, and preferably the applied RF alternating voltage, across a frequency interval (e.g. of 0 to 2000 MHz). For instance, the curve of a Bode plotter could be analyzed or in general Bode plotter results, in other words the ratio of the amplitude and the phase of an input and an output signal across the said frequency interval (e.g. 150 MHz to 2 GHz). The upper frequency of the frequency interval can also be larger than 1 GHz, for instance.

According to a preferred measuring method, the frequency of the RF alternating voltage is greater than 50 MHz, preferably greater than 100 MHz, but in particular less than 2 GHz. To this end it should be noted that a single frequency (in other words an alternating voltage with a single frequency) does not necessarily have to be applied. In practice it is not possible to irradiate a single frequency, but instead always a frequency interval of a specific width. In practice the central frequency of such an interval is considered to be the main frequency. This main frequency is meant here. An RF alternating frequency with a number of main frequencies (modes) can feasibly be irradiated in order to excite different resonances in the bearing. To this end it is in particular preferred that at least two main frequencies or even at least 5 main frequencies are irradiated (or the RF alternating voltage has this main frequency).

According to a preferred measuring method, the inductance LFM of the liquid metal portion is first determined from the measured inductance of the liquid metal slide bearing or a variable associated with the inductance. Here the previously known inductances of the inner bearing part and the outer bearing part can be deducted from the measured inductance, for example. The variable n is then determined with predetermined inductance values $L_i$ of at least of one structural element on the basis of the formula (3)

$$\left(\frac{1}{L_S} = \sum_1^n \frac{1}{L_i}\right).$$

An integral approach is also possible however, in which no total, but instead a function for calculating LS is used.

Here a low fill level means therefore that fewer structural elements connected in parallel exist and a high fill level means that more structural elements connected in parallel exist, wherein the structural elements represent purely theoretical elements for describing the bearing.

According to a preferred measuring method, a calibration to a liquid metal slide bearing which is constructed in the same way as the measured liquid metal slide bearing is carried out before determining the quantity of liquid metal. This bearing (reference bearing) which is constructed in the same way is in particular completely filled. The reference bearing (the liquid metal slide bearing which is constructed in the same way) is preferably measured for the calibration by means of fluoroscopy, particularly preferably by means of an electron accelerator system scan. The reference bearing can then be measured with the inventive measuring method and the thus determined value of the leakage inductance then represents the reference for a maximum of the fill quantity for all measurements to be compared. Different reference bearings with different fill levels can naturally also be measured, namely initially precisely (e.g. SILAC) for determining the precise fill level, and then with the inventive method for obtaining a reference variable. If an unknown bearing is now measured with the inventive method, these measured values can be compared with the reference values in order to obtain a measure of the fill level of the measured bearing.

According to a preferred measuring method, a further measurement of the quantity of liquid metal, in particular if the determined quantity of liquid metal lies below a previously defined limit value, is carried out on the basis of the determination of the quantity of liquid metal on the liquid metal slide bearing. This further measurement is carried out here by means of another measuring method, preferably by means of fluoroscopy of the liquid metal slide bearing, particularly preferably by means of an electron accelerator system scan. In this way the inventive measuring method can initially determine very quickly and easily whether a bearing is filled optimally and if the filling is not determined to be optimum, the bearing is checked with a more precise yet more elaborate measuring method. With the aid of the inventive measuring method, a preselection can therefore be made for instance to determine whether or not an electron accelerator system scan is worthwhile. If the inventive measuring method were applied in the vacuum of the slide bearing fill level, a statement could be made as to whether the fill process was successful or whether it has to be continued.

A preferred measuring device comprises a control unit for controlling a measuring apparatus, which carries out a different measuring method to the measuring device, preferably by means of fluoroscopy of the liquid metal slide bearing, particularly preferably by means of an electron accelerator system scan. A measurement by means of the measuring apparatus is started and/or evaluated by means of the measuring device, for instance.

According to a preferred embodiment, within the scope of determining the resonance frequency, further information is derived from the measuring results in addition to purely determining the resonance frequency. The curve shape of the resonance curve is preferably examined here further, e.g. according to further resonance frequencies (secondary peak) or deflections in the curve shape from a pure resonance curve with a single resonance frequency. In addition, the amplitude of the resonance frequency can be examined. Therefore, after comparison with examination results on bearings, which were filled with different quantities of liquid metals, it is thus possible to establish the points at which liquid metal is missing. This lies in the fact that with a real bearing the cross-section in the various bearing regions is different. Therefore different resulting inductances Li are formed (see formula 2) for the different regions. This essentially lies in the fact that the current has to overcome surfaces of different sizes at different points in the bearing. A separation of imperfections in the axial bearing compared with imperfections in the radial bearing can therefore take place. A Fourier transformation of the resonance curve preferably takes place within the scope of the determination.

A rotary anode x-ray tube is shown in FIG. 1, which has a rotary anode 1, which is accommodated in a vacuum piston 2. The vacuum piston 2 also contains in a manner known per se a cathode 3, which contains one or more here invisible electron emitters in a focus head 4.

In order to ensure the rotatable bearing of the rotary anode 1, a liquid metal slide bearing 6 is provided, which, as an inner bearing part 7, has a bearing axis connected fixedly to the vacuum piston 2. The anode disk 5 of the rotary anode 1 is fixedly attached to the rotating outer bearing part 8. A bearing flange 9 prevents liquid metal from escaping out of the bearing.

Figure 2:
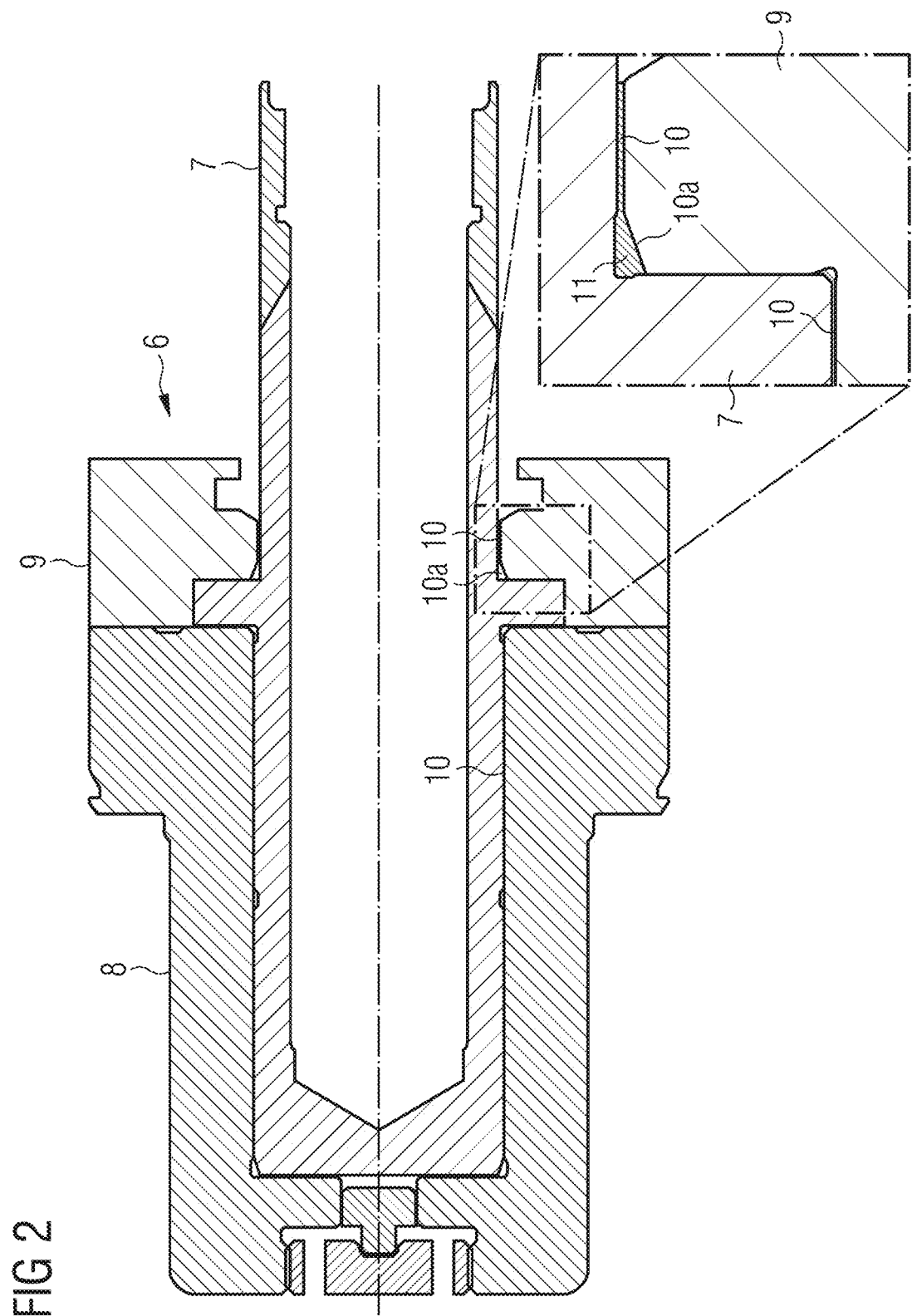

FIG. 2 shows a longitudinal section through a liquid metal slide bearing 6, such as could be installed for instance in a rotary anode according to FIG. 1. The liquid metal slide bearing 6 comprises an inner bearing part 7, an outer bearing part 8 and a bearing gap 10 between these bearing parts 7, 8. A bearing flange 9 prevents liquid metal 11 from escaping out of the bearing gap 10. An enlargement of the bearing gap 10 which is filled with liquid metal 11, i.e. a metal which is already liquid at room temperature, is visible to the bottom right. The bearing gap 10 is a few μm wide at its narrow points but has here also thicker regions which are used as a reservoir 10a for liquid metal 11.

Figure 3:
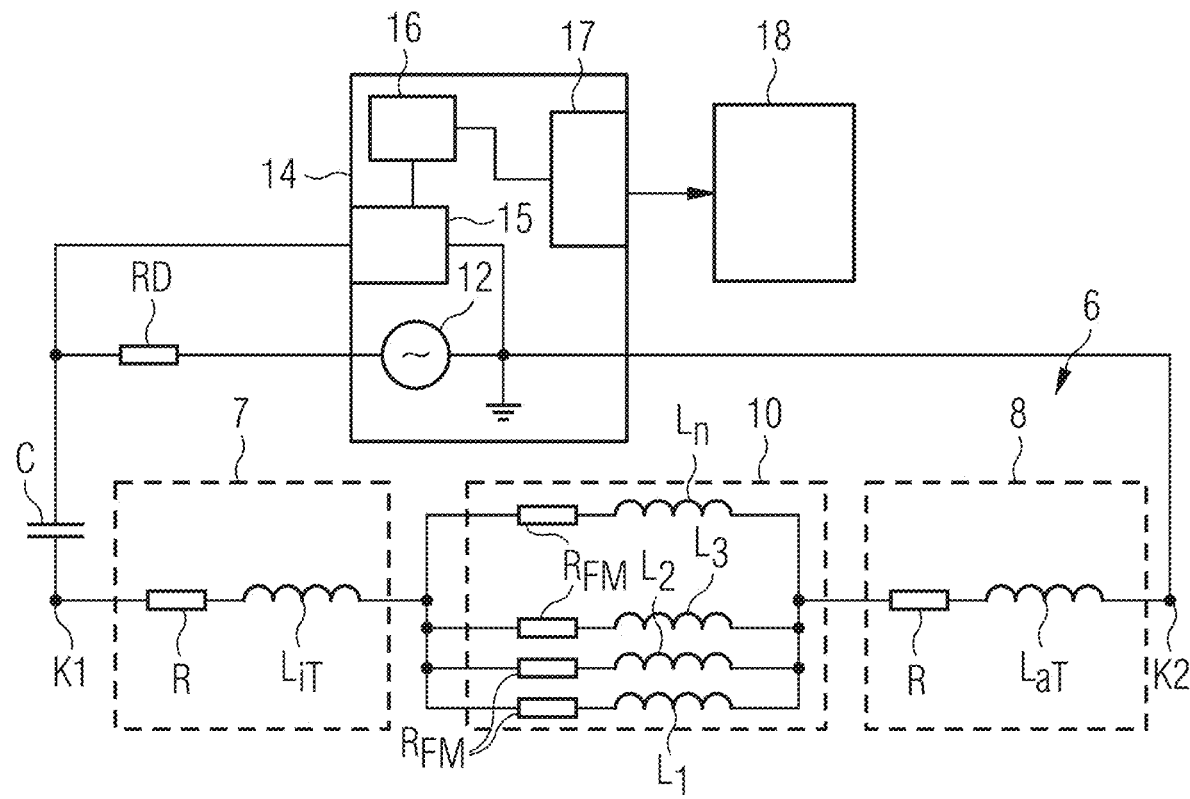

FIG. 3 shows a switching example for a model of the invention. The electronic components shown such as resistances R, capacitances C and inductances $L_{iT}$, $L_{aT}$, $L_1$, $L_2$, $L_3$, $L_n$ are generally not present as real components, but instead represent electrical properties (structural elements) of the liquid metal slide bearing 6, as shown in FIG. 2, for instance.

The liquid metal slide bearing 6 is shown below in the form of a schematic equivalent circuit diagram. The liquid metal slide bearing 6 has a series of series connections comprising an inductance $L_{iT}$, $L_{aT}$, $L_1$, $L_2$, $L_3$, $L_n$ and an ohmic resistance R of the bearing parts 7, 8 and $R_{FM}$ of the liquid metal 11 (the resistance only plays a subordinate role here).

These series connections can also be referred to as "structural elements", since they are not actually present but instead describe electrical properties of the bearing. In the equivalent circuit diagram, the inner bearing part 7 has an inductance $L_{iT}$ and the outer bearing part 8 has an inductance $L_{aT}$ in the equivalent circuit diagram. As the equivalent circuit diagram the bearing gap 10 has a parallel connection of the same or different inductances $L_1$, $L_2$, $L_3$, $L_n$. The higher the liquid metal portion in the bearing gap 10, the more inductances $L_1$, $L_2$, $L_3$, $L_n$ there are present. The inner bearing part 7, the outer bearing part and the bearing gap 10 form a series connection with respect to the equivalent circuit diagrams.

A measuring device 14 according to a preferred embodiment is shown above. The measuring device 14 comprises an RF unit 12 (e.g. an RF generator 12) designed to apply an RF alternating voltage between electrical contacts K1, K2 to different bearing parts 7, 8 (to the contact K1 on the outer bearing part 8 and the contact K2 on the inner bearing part 7) with a predetermined irradiation frequency range, a measuring unit 15 designed to measure an RF signal S (see e.g. FIG. 5) on two electrical contacts K1, K2 on the different bearing parts 7, 8 and a determination unit 16 designed to determine the quantity of liquid metal on the basis of the measured RF signal S.

In addition, the measuring device further comprises a control unit 17. This control unit 17 controls a measuring device 18, e.g. an electron accelerator system, in particular a SILAC scanner, which carries out another measuring method than the measuring device 14. In this way for example a fluoroscopy of a measured liquid metal slide bearing 6 can take place automatically if the measurement indicates problems in the liquid metal portion.

The damping resistance RD (e.g. with 100 ohm) separates the signal source (RF unit 12) from the liquid metal slide bearing 6 and the measuring device 14. In the series resonance, the current flow through the real part generates a drop in voltage by way of this damping resistance RD. The voltage minimum compared with the signal source can be measured. The resistance increases with a parallel resonance, there is a minimum current which in turn appears as a drop in voltage by way of the damping resistance RD. Damping resistances RD of 50 ohm are often also used in practical RF applications.

Reference is made here to this circuit diagram, in particular the parts which represent an equivalent circuit diagram, only being shown by way of example. Therefore it would also be possible for example to add line impedances, impedances of probe heads or termination impedances. For improved clarity all these components were omitted here.

Since the height of the liquid metal state in the bearing gap 10 corresponds to a number of N inductances connected in parallel $L_1$, $L_2$, $L_3$, $L_n$ and the resonance frequency is dependent on these inductances $L_1$, $L_2$, $L_3$, $L_n$, the resonance frequency can be determined from the position. The higher the fill level, the greater n and the greater the resonance frequency. In order to confirm the measurement or to determine the precise degree of the filling, the control unit 17 can now switch on the measuring apparatus 18 and carry out a (slow but on the other hand more precise) measurement with this measuring apparatus 18.

In practice the overall inductance $L_{iT}$, $L_{aT}$, $L_1$, $L_2$, $L_3$, $L_n$ of a liquid metal slide bearing 6 is very small (nH range). The RF unit 12 must therefore be operated with VHF frequencies or UHF frequencies.

Figure 4:
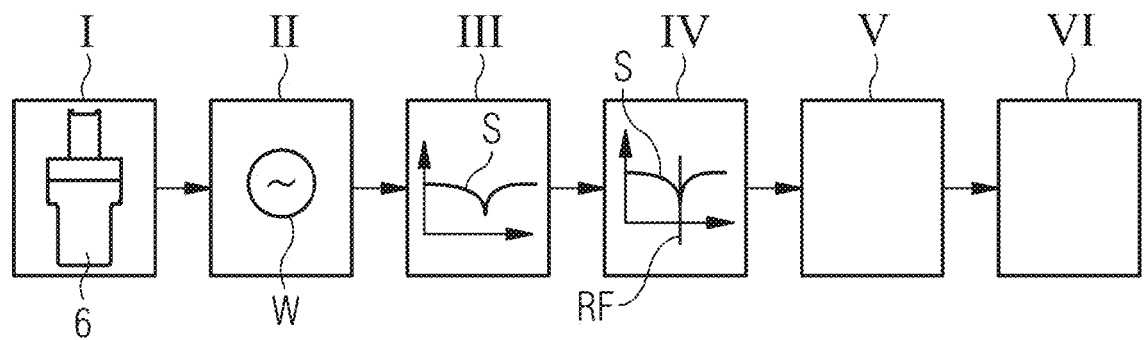

FIG. 4 shows a block diagram for a possible course of an inventive measuring method for a liquid metal slide bearing 6.

In step I, a liquid metal slide bearing 6 (see e.g. FIG. 2) to be measured is provided, which has two bearing parts 7, 8, between which the liquid metal 11 is arranged. A corresponding measuring device is connected to the liquid metal slide bearing 6, as shown in FIG. 3.

In step II, an RF alternating voltage between electrical contacts K1, K2 is applied to different bearing parts 7, 8. Here the RF alternating voltage has a predetermined irradiation frequency range.

In step III, an RF signal S is measured on electrical contacts K1, K2 of different bearing parts 7, 8.

In step IV, a resonance frequency RF is determined from the measured RF signal S.

In step V the quantity of liquid metal is determined on the basis of the resonance frequency RF, e.g. by taking into account the formulae (1)

$$f_R = \frac{1}{2\pi\sqrt{L_G C_K}}$$

and (3)

$$\frac{1}{L_S} = \sum_1^n \frac{1}{L_i}.$$

In step VI, a further measurement of the quantity of liquid metal takes place on the basis of the determination of the quantity of liquid metal (here e.g. the determined quantity of liquid metal is below a previously defined limit value) on the liquid metal slide bearing 6. This measurement takes place here by means of another measuring method, e.g. by means of fluoroscopy of the liquid metal slide bearing 6 which can be carried out by means of a SILAC scan.

Figure 5:
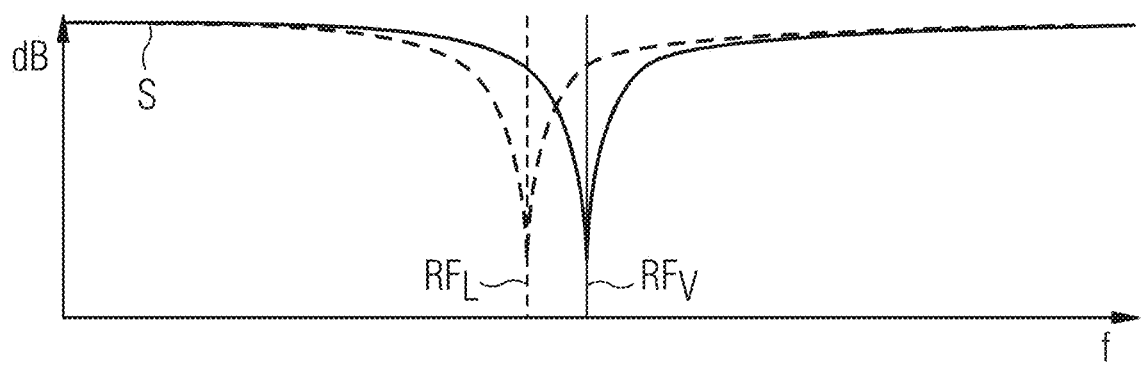
Figure 5:
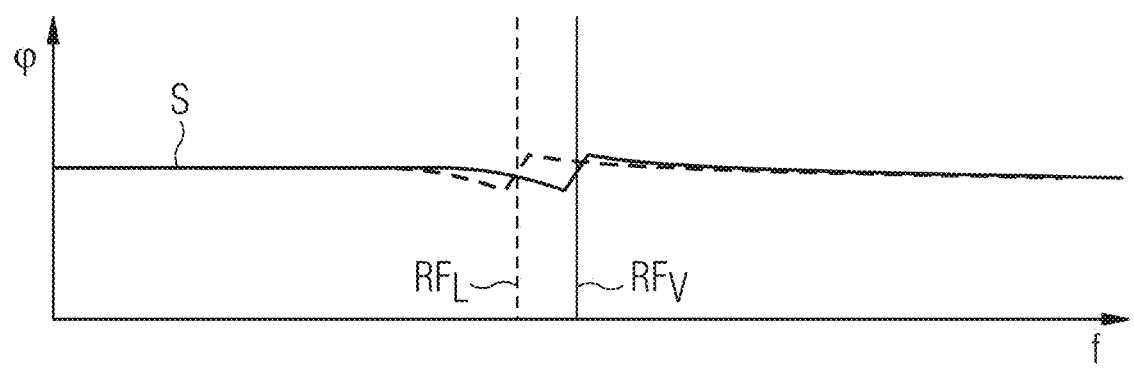

FIG. 5 shows a representation of possible RF signals plotted against the frequency f. The amplitude of the signal is specified above in respect of its damping in dB, a Bode plot which represents the phase relating to the input signal (RF alternating voltage) is specified below.

Two RF signals S are shown here in each case. One with a full liquid metal slide bearing 6 (continuous line) and another with an empty liquid metal slide bearing (dashed line). The resonance frequency $RF_V$ with a full liquid metal slide bearing 6 is clearly higher than the resonance frequency $RF_L$ with an empty liquid metal slide bearing 6. The degree of the deviation from the resonance frequency $RF_V$ with a full liquid metal slide bearing 6 is a measure of the quantity of liquid metal in the liquid metal slide bearing 6. An accurate correlation can be achieved by reference measurements on liquid metal slide bearings 6 with a known fill level.

Finally, it should also be noted that the measuring method or the measuring device described above in detail and the liquid metal slide bearing disclosed are merely example embodiments which can be modified by a person skilled in the art in a variety of ways without departing from the scope of the invention. In addition, the use of the indefinite article "a" or "an" does not preclude the relevant features also being present plurally. Similarly, the expressions "unit" and "device" do not preclude the components in question from consisting of a plurality of cooperating partial components with can also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A measuring method for a liquid metal slide bearing, comprising:
   providing a liquid metal slide bearing to be measured, the liquid metal slide bearing including two bearing parts with liquid metal being arranged between the two bearing parts;
   measuring inductance, or a variable associated with the inductance, of the liquid metal slide bearing; and
   determining a quantity of liquid metal in the liquid metal slide bearing based upon the inductance, or the variable associated with the inductance, measured.

2. The measuring method of claim 1, further comprising:
   applying a radio frequency (RF) alternating voltage between electrical contacts to different bearing parts, of the two bearing parts, within a frequency range;
   measuring an RF signal on the electrical contacts on the different bearing parts; and
   determining the quantity of liquid metal based upon the RF signal measured.

3. The measuring method of claim 2, further comprising:
   determining a resonance frequency from the measuring of the RF signal; and
   determining the quantity of liquid metal based upon the resonance frequency determined.

4. The measuring method of claim 2, further comprising:
   determining a minimum or a maximum of a bearing impedance from the measuring of the RF signal; and
   determining the quantity of liquid metal based upon the bearing impedance determined.

5. The measuring method of claim 2, wherein the quantity of liquid metal is determined based upon a ratio of an amplitude and a phase of the RF signal measured, and the RF alternating voltage applied is determined across a frequency interval.

6. The measuring method of claim 2, wherein a frequency of the RF alternating voltage lies in one of a very high frequency (VHF) range and an ultra high frequency (UHF) range.

7. The measuring method of claim 1, wherein an inductance $L_{FM}$ of a liquid metal portion is determined from the inductance of the liquid metal slide bearing, or the variable associated with the inductance of the liquid metal slide bearing, measured and wherein the variable is determined with inductance values $L_i$ of at least one structural element based upon $$\frac{1}{L_{FM}} = \sum_{1}^{n} \frac{1}{L_i},$$

wherein n is the variable associated with the inductance of the liquid metal slide bearing and the at least one structural element represents an element for describing the bearing.

8. The measuring method of claim 1, wherein before the determining of the quantity of liquid metal, liquid metal slide bearings constructed in a same way are calibrated to the liquid metal slide bearing to be measured.

9. The measuring method of claim 1, wherein based upon the determining of the quantity of liquid metal, a further measurement of the quantity of liquid metal takes place on the liquid metal slide bearing by way of another measuring method.

10. The method of claim 9, wherein the further measurement of the quantity of liquid metal takes place on the liquid metal slide bearing by way of fluoroscopy of the liquid metal slide bearing.

11. The measuring method of claim 1, further comprising:
applying a radio frequency (RF) alternating voltage between electrical contacts to different bearing parts, of the two bearing parts, within a frequency range;
measuring an RF signal on the electrical contacts on the different bearing parts;
determining a resonance frequency from the measuring of the RF signal; and
determining the quantity of liquid metal based upon the resonance frequency determined.

12. The measuring method of claim 11, wherein the quantity of liquid metal is determined based upon a ratio of an amplitude and a phase of the RF signal measured, and the RF alternating voltage applied is determined across a frequency interval.

13. The measuring method of claim 1, further comprising:
applying a radio frequency (RF) alternating voltage between electrical contacts to different bearing parts, of the two bearing parts, within a frequency range;
measuring an RF signal on the electrical contacts on the different bearing parts;
determining a minimum or a maximum of a bearing impedance from the measuring of the RF signal; and
determining the quantity of liquid metal based upon the bearing impedance determined.

14. The measuring method of claim 13, wherein the quantity of liquid metal is determined based upon a ratio of an amplitude and a phase of the RF signal measured, and the RF alternating voltage applied is determined across a frequency interval.

15. A measuring device for a liquid metal slide bearing including two bearing parts, liquid metal being arranged between the two bearing parts, the measuring device comprising:
a measuring unit, designed to measure inductance of the liquid metal slide bearing or a variable associated with the inductance; and
a determination unit, designed to determine a quantity of liquid metal in the liquid metal slide bearing based upon the inductance, or the variable associated with the inductance, measured.

16. The measuring device of claim 15, further comprising:
a radio frequency (RF) unit, designed to apply an RF alternating voltage between electrical contacts to different bearing parts, of the two bearing parts, within a frequency range, wherein the measuring unit is designed to measure an RF signal on the electrical contacts on the different bearing parts and wherein the determination unit is designed to determine the quantity of liquid metal based upon the RF signal measured.

17. The measuring device of claim 15, further comprising:
a control unit, designed to control a measuring apparatus, to carry out another measuring method different from the measuring device.

18. The measuring device of claim 17, wherein the another measuring method different from the measuring device, includes fluoroscopy of the liquid metal slide bearing.

19. A liquid metal slide bearing comprising:
an inner bearing part; and
an outer bearing part, a bearing gap between the inner bearing part and the outer bearing part being filled with liquid metal, wherein the liquid metal slide bearing is configured with contacts designed for connecting with the measuring device of claim 15.

20. An x-ray tube, comprising:
a rotary anode, rotatably mounted via the liquid metal slide bearing of claim 19.

21. An apparatus, comprising:
the liquid metal slide bearing of claim 19 and the measuring device.

* * * * *